(12) United States Patent
Kraft et al.

(10) Patent No.: US 8,822,947 B2
(45) Date of Patent: Sep. 2, 2014

(54) PARTICLE BEAM GENERATING DEVICE

(75) Inventors: Gerhard Kraft, Darmstadt (DE); Nami Saito, Darmstadt (DE); Dieter Schardt, Darmstadt (DE)

(73) Assignee: GSI Helmholzzentrum fuer Schwerionenforschung GmbH, Darmstadt (DE)

( * ) Notice: Subject to any disclaimer, the term of this patent is extended or adjusted under 35 U.S.C. 154(b) by 0 days.

(21) Appl. No.: 13/805,676

(22) PCT Filed: May 26, 2011

(86) PCT No.: PCT/EP2011/058621
§ 371 (c)(1),
(2), (4) Date: Dec. 20, 2012

(87) PCT Pub. No.: WO2011/160915
PCT Pub. Date: Dec. 29, 2011

(65) Prior Publication Data
US 2013/0092839 A1  Apr. 18, 2013

(30) Foreign Application Priority Data
Jun. 23, 2010  (EP) ..................... 10006501

(51) Int. Cl.
*G21K 5/04* (2006.01)
*G21K 5/10* (2006.01)
*G21K 5/02* (2006.01)
*A61B 6/00* (2006.01)
*A61N 5/10* (2006.01)

(52) U.S. Cl.
CPC ........... *G21K 5/10* (2013.01); *A61N 2005/1087* (2013.01); *G21K 5/04* (2013.01); *A61N 5/1049* (2013.01); *G21K 5/02* (2013.01); *A61N 5/1043* (2013.01); *A61N 2005/1054* (2013.01); *A61N 5/1077* (2013.01); *A61B 6/00* (2013.01)
USPC .. 250/423 R; 250/424; 250/427; 315/111.01; 315/111.81; 315/111.91

(58) Field of Classification Search
USPC .......... 250/423 R, 424, 425, 426, 427, 423 P, 250/423 F, 492.3; 315/111.01, 111.81, 315/111.91
See application file for complete search history.

(56) References Cited

U.S. PATENT DOCUMENTS

| | | |
|---|---|---|
| 2004/0096033 A1 | 5/2004 | Seppi et al. |
| 2007/0181831 A1* | 8/2007 | Tokuda et al. ........... 250/492.21 |
| 2012/0328066 A1* | 12/2012 | Burke et al. .................. 376/111 |

FOREIGN PATENT DOCUMENTS

| | | |
|---|---|---|
| EP | 2088613 A1 | 8/2009 |
| EP | 2096663 A2 | 9/2009 |
| WO | 2005110495 A1 | 11/2005 |

OTHER PUBLICATIONS

Sistema Aqua Advanced Quality Assurance Per Il Centro Nazionale Di Adroterapia Oncologica, Documento preparato dalia Fondazione TERA, Feb. 15, 2008, p. 1-134.

(Continued)

*Primary Examiner* — Nicole Ippolito
(74) *Attorney, Agent, or Firm* — Leydig, Voit & Mayer, Ltd.

(57) ABSTRACT

A particle beam generating device includes at least one accelerator unit for generating a particle beam and at least one emission unit for the output of the at least one particle beam onto a workpiece. The device is configured to release at least two particle beams including hadronic particles with at least one of a different mass or a different charge.

17 Claims, 5 Drawing Sheets

(56) References Cited

OTHER PUBLICATIONS

Peach et al., Pamela—a model for an FFAG based hadron therapy machine, Proceedings of the 2001 Particle Accelerator Conference, Jun. 25, 2007 IEEE, Chicago, pp. 2880-2882.

Schlitt et al, Linac Commissioning at the Italian Hadrontherapy Centre CNAO, Proceedings of IPAC'10, Kyoto, Japan, Jun. 1, 2010, pp. 27-69.

Schulte et al., Design of a proton computed tomography system for applications in proton radiation therapy, 2003 IEEE Nuclear Science Symposium Conference Record. / 2003 IEEE Nuclear Science Symposium and Medical Imaging Conference. Portland, OR, Oct. 19-25, 2003, pp. 1579-1583.

Holdford, Introduction to Focused Ion Beams, Chapter 6 (The uses of dual beam fib in microelectronic failure analysis), Introduction to focused ion beams : instrumentation, theory, techniques and practice, Nov. 1, 2004 Springer, New York, pp. 107-109.

European Patent Office, International Search Report in International Patent Application No. PCT/EP2011/058621 (Sep. 6, 2011).

\* cited by examiner

PARTICLE BEAM GENERATING DEVICE

CROSS REFERENCE TO RELATED APPLICATIONS

This application is a U.S. National Phase application under 35 U.S.C. §371 of International Application No. PCT/EP2011/058621, filed on May 26, 2011, and claims benefit to European Patent Application No. EP 10 006 501.0, filed on Jun. 23, 2010. The International Application was published in English on Dec. 29, 2011 as WO 2011/160915 under PCT Article 21 (2).

FIELD

The invention relates to a particle beam generating device, comprising at least one accelerator unit for generating a particle beam and at least one emission unit for the output of said at least one particle beam onto a workpiece. The invention further relates to a method for controlling a particle beam device. In nowadays technology, a variety of different material is irradiated by some form of radiation for processing said material in a certain way. For example, by irradiating some particular material, the characteristics of said material can be altered in a desired way. As an example, by irradiating a workpiece made of a suitable material, the surface of said workpiece can be modified or structured.

BACKGROUND

Depending on the material and the workpiece to be treated, a wide variety of different types of radiation can be used. For example, radiation from the electromagnetic spectra can be used. The wavelength can differ in a wide range and can be, as an example, chosen from the radiomagnetic spectra, the infrared spectra, the visible spectra, the ultraviolet spectra up to the x-ray spectra and even higher. Another possible form of irradiating workpieces is in the form of particle irradiation, in particular in the form of accelerated particle beams. The particles themselves can be chosen from a wide variety as well. As an example, leptons like electrons or positrons can be used. Also hadronic particles can be used like protons, light ions (for example protons, ionized helium atoms) as well as heavy ions (for example carbon ions, oxygen ions and neon ions). Other possible hadronic particles are pions, mesons and so on. The possible energies for such particles can vary from low energies like several kilo electron volts up to speeds close to the speed of light with energies in the range of several hundred mega electron volts, or even in the giga electron volts range.

Whereas a possible application for irradiating material lies in applications, where the workpiece to be treated has to be irradiated in a uniform way, for example when a material has to be modified by irradiation other applications exist, where the irradiation has to be applied with a certain pattern. One technological field, where such patterned irradiation is necessary is the production of microprocessors or nanomechanics. Here, certain parts of the surface of the workpiece to be treated have to be irradiated, while other parts should not be irradiated at all. This is done by using patterned masks, which are irradiated by a homogeneous radiation source. Another possible way of applying such structured radiation is to use a pencil-like beam and to move the spot of said beam across the surface of the workpiece in a particular pattern.

Nowadays, not only two-dimensional treatment of workpieces is performed, but also three-dimensional irradiation of workpieces. This way, it is even possible to deposit a certain radiation dose inside the workpiece without opening said workpiece. Hence, a treatment of a three-dimensional section within a workpiece is possible.

Another complexity arises, when a moving workpiece or a workpiece with moving parts has to be treated. Here, the application of an irradiation has to be performed in a way that the movements of the body are considered when irradiating said workpiece. This is frequently referred to as a four-dimensional application of radiation (where time is considered to be the fourth dimension).

A movement of the workpiece cannot only occur with respect to an external reference frame, but can also occur by relative movements of parts of said workpiece against other parts of said workpiece. Therefore, rotational deformations, longitudinal deformations and quenching of material have to be considered.

Of course, not only inorganic material can be treated by applying radiation, in particular particle beams. It is also possible to treat organic matter and even living tissue of animals and human beings. One possible application for three-dimensional or four-dimensional application of radiation is the treatment of cancer. Here, a certain area of the human body in particular the tissue, which is infected by tumour cells, has to be treated with a certain irradiation dose, so that the cells within this volume are destroyed or at least damaged. Of course, the surrounding healthy tissue should be protected by applying very little radiation, if at all.

If particular, for the treatment of tumours, particle beams, in particular hadronic particle beams (even more preferably heavy ion particle beams) have proven to be very useful. This is because particle beams show a pronounced so-called Bragg-peak. That is, the energy of a particle, moving through tissue, is not deposited equally over the particle's path. Instead, the majority of the particle's energy is transferred in the very last part of the path, before the respective particle gets stuck.

An problem when treating three-dimensional structures, in particular human beings with individual characteristics, is that first the areas, where the radiation has to be deposited, has to determined. This should be done by methods, which do not need to open the workpiece, in particular a patient having the tumor, to be treated (so-called non-invasive methods), because otherwise the advantage of three-dimensionally structured radiation would be lost.

For performing this task, usually three-dimensional imaging techniques (or even four-dimensional imaging techniques, taking into account movements) are used. Examples of such techniques are ultrasonic imaging techniques or computer tomography methods. However, these methods show disadvantages as well. With computer tomography, a major disadvantage is that an additional radiation dose is applied to the body. In particular, when a four-dimensional image has to be taken and/or a continuous imaging during the treatment itself is needed, this additional radiation dose can be substantial. Therefore, there is a tendency to reduce the additional radiation level as far as possible.

The disadvantage of applying an additional dose can be avoided by using ultrasonic imaging techniques. However, the image quality is sometimes far from perfect. Another major disadvantage of ultrasonic imaging techniques is that they cannot be used during the treatment with hadronic particles at all.

A possible way out is to use the above mentioned imaging techniques (or even other methods) and to link the thus determined movements to so-called movement substitutes. This can be achieved by correlating the three-dimensional pictures, gained by computer tomography or ultrasonic imaging techniques to a substituting signal, like the picture of a standard video camera or a signal from a length measuring strap, which is attached to a patient's chest or the like. Although such substitutes work relatively well in practice, the maximum resolution achievable is limited.

Another disadvantage, not yet mentioned is that the density of the tissue, as seen by the particles (and hence the penetration length of the particles) can be substantially different from the density of tissue, as seen by leptonic particles, phonons (ultra sonic imaging techniques) or photons (x-ray imaging techniques). Experiments have shown that this gives rise to sometimes substantial errors.

Hence, there is still a necessity for a method on how to determine distinct features within a workpiece or a body and/or the movement of different regions of the workpiece or the body (in particular the body of a patient) during the treatment of said workpiece or body.

SUMMARY

In an embodiment, the present invention provides a particle beam generating device including at least one accelerator unit for generating a particle beam and at least one emission unit for the output of the at least one particle beam onto a workpiece. The device is configured to release at least two particle beams including hadronic particles with at least one of a different mass or a different charge.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
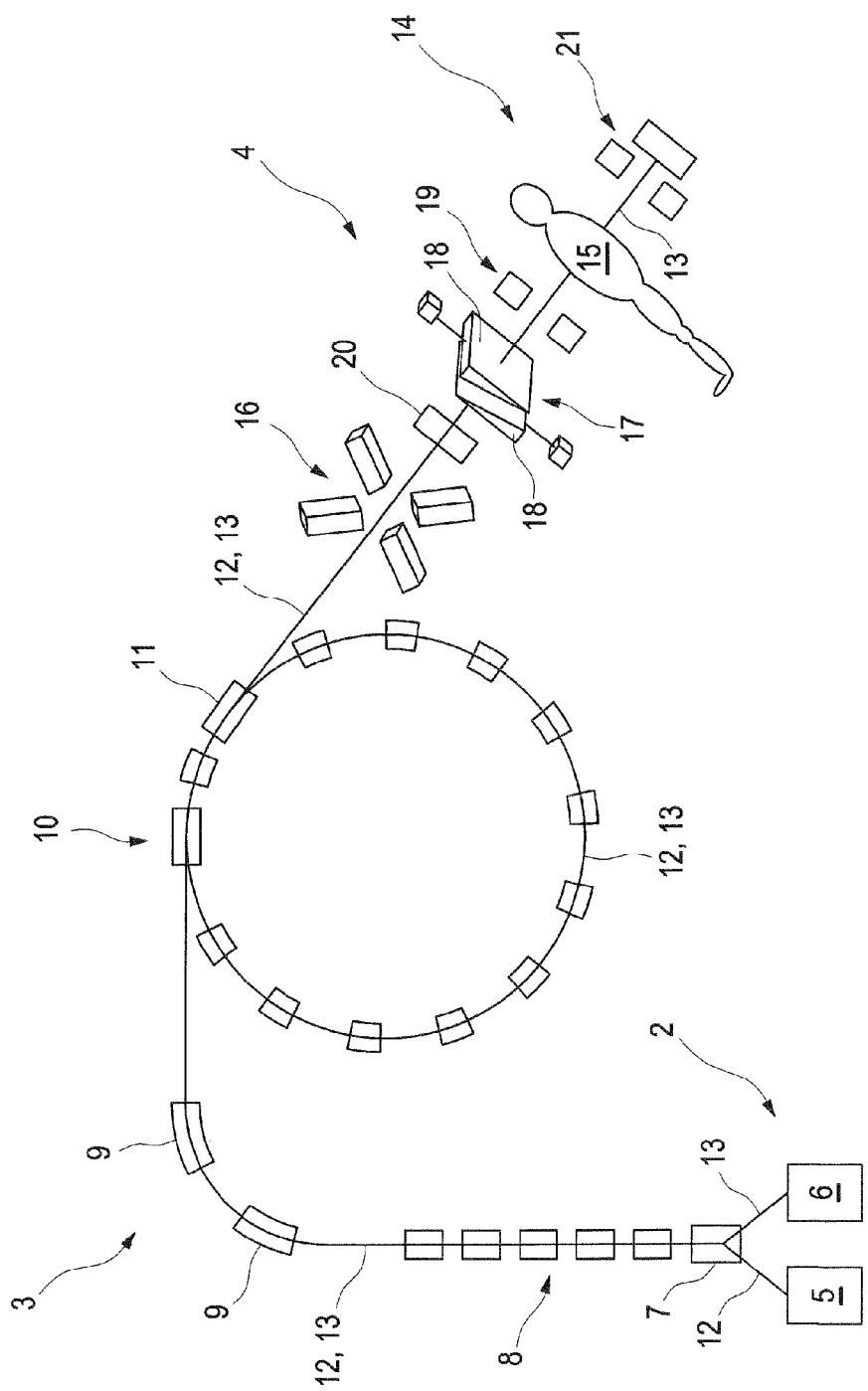
FIG. 1 shows a schematic overview of a particle beam generating device.

An aspect of the invention is to provide a particle beam generating device that is advantageous over existing particle beam generating devices. Another aspect of the invention is to provide a method for controlling a particle beam generating device that is advantageous over existing methods for controlling a particle beam device.

An embodiment of the invention provides a particle beam generating device, comprising at least one accelerator unit for generating at least one particle beam and at least one emission unit for the output of said at least one particle beam onto a workpiece in a way that at least in part and/or at least at times at least two particle beams of a different type are released. As an accelerator unit, in principle all existing designs of particle accelerators can be used. In particular, linear accelerators (linac), cyclotrons, synchrotrons and the like can be used. The particle beams do not have to be emitted constantly. For example, using a synchrotron, generating a continuous beam would not be possible.

Hence, an intermittent beam or the like is encompassed with respect to the invention as well. Furthermore, the two particle beams (or even more particle beams) can differ with their output characteristics as well. For example, the first particle beam can be continuous, while the second particle beam can be intermittently emitted (or vice versa). Even if two or more particle beams are emitted intermittently, the output characteristics can differ (for example the fraction of the lengths of the emission interval versus the non-emission interval can vary). By the wording "particle beams of a different type", in particular the type and/or characteristics of the particles, forming the respective particle beam are meant. For example, a first particle beam can comprise electrons, while a second particle beam may comprise hadronic particles. Also, it is possible that two or more particle beams comprise hadronic particles, while the mass, the charge, the energy or the like of the two particles fractions may differ. Furthermore, a mixture of nucleonic particles (in particular ions) and/or mesons and/or pions is possible as well.

Furthermore, the two (or even more) particle beams can impinge onto the workpiece (at least in part and/or at least at times) from the same direction and/or from different directions. By the notion "workpiece", not only inorganic matter is encompassed. Instead, organic material, including organic living tissue can be treated as well. Even more, the treatment of living animals and/or human beings can even be a preferred application for the particle beam generating device. The at least two particle beams of a different type can in particular be released by the of least one emission unit.

The particle beam generating device can for example be applied for the investigation of moving parts of a motors, wherein the investigations are per-formed to detect tribological changes inside the motor (non-destructive investigations).

Alternatively or additionally, it is possible to design a particle beam generating device, comprising at least one accelerator unit for generating at least one particle beam, at least one emission unit for the output of said at least one particle beam onto a workpiece that is at least in part moving with time and at least one detector device for detecting said at least one particle beam, and wherein said at least one detector device is preferably arranged down-stream to said workpiece, in a way that the information, gained by said at least one detector device is used at least in part and/or at least at times for determining the current position of at least part of said workpiece. On a very basic level, this can be considered to be a device that is quite similar to the above described particle beam generating device. However, only a "monitoring particle beam" ("second particle beam") is used, while a "treatment particle beam" ("first particle beam") is not necessarily present. Contrary to the state of the art, where a similar method and/or device is only used to (if at all) verify a specific location of the workpiece (which is known as "proton radiography", for example), the device is presently used for monitoring (measuring) the movement of a moving workpiece and/or a moving part of the (potentially moving) workpiece. This, of course, necessitates a relatively fast device, which—according to the state of the art—was supposed to be technically and/or economically not feasible. Using the suggested device, however, it is possible to provide for a relatively simple, yet quite precise method for determining the movement of (parts within) a workpiece. In particular, the particles of the particle beam can be chosen in a way that the particles that are used for measurement are "seeing" the workpiece in the same way as a potentially later applied treatment particle beam (as an example) does. Although at first hand, the device necessary for doing this seems to be pretty elaborate and expensive, it should be noted that it is usually possible to use already present components to a large extent. Hence, the overall additional effort is usually quite low. In particular, the measurements derived can be used as some kind of "movement substitute". Preferably, at least one of the detectors used (particularly at least one of the detectors downstream to the workpiece) is designed to be an energy detecting device. Using such a device, it is possible to derive the energy loss of the particles of the particle beam within the workpiece, which is usually a good indication for the actual movement/position status.

Preferably, the particle beam generating device can be designed in a way that at least one of said particle beams, preferably at least two of said particle beams, more preferably a plurality of said particle beams, most preferably all of said particle beams contain hadronic particles and/or charged particles, preferably nucleonic particles and/or positively charged particles. The afore-mentioned types of particles are preferred, because those particles usually show a particularly profound Bragg-peak. Therefore, a three-dimensional dose, to be applied to the inner volume parts of the workpiece can be applied very sharply and exactly defined. In principle such a behaviour is particularly preferred for a processing particle beam. However, if a monitoring particle beam uses somewhat similar types of particles, the density of the material to be penetrated, as seen by the respective particles, can be quite close together. Therefore, the behaviour of the different particle beams resemble each other, although the exact behaviour can differ.

Preferably, the particles, contained in at least two of said particle beams comprise a different mass and/or a different charge and/or a different energy. This way, the principal behaviour of the respective particle beams can be similar to each other, while the exact behaviour is different. This way, it is possible, for example, that one particle beam has the maximum of its Bragg-Peak within the workpiece and "gets stuck" inside the workpiece, while a second particle beam (while showing a principally similar behaviour) is still able to penetrate and leave the workpiece downstream to the workpiece. This way, the second particle beam can be measured after passing the workpiece. In particular, it is possible to use carbon ions, oxygen ions and/or neon ions for a first particle beam, while for a second particle beam, protons and/or helium ions can be used.

Even more preferred, the particle beam generating device can be designed in a way that at least a first one of said particle beams is a processing particle beam, used for processing purposes, while at least a second one of said particle beams is a monitoring particle beam, used for monitoring purposes. This way, the processing particle beam can be essentially used for depositing a certain dose within the workpiece (or parts of it). Even complex three-dimensional patterns can be accomplished by using scanning techniques, in particular raster scanning techniques. The monitoring particle beam can be primarily used for monitoring the processing process. In particular, the monitoring particle beam can be used for gaining information about the exact location of a certain part within the workpiece (for example a tumour within a patient) and/or for monitoring movements of the workpiece or parts of the workpiece. This information can be used for modifying the processing process itself, thus usually resulting in a better quality of the treatment.

Even more preferred, said particle beam generating device can comprise at least one detector device for detecting at least one of said particle beams. Preferably, said particle beam generating device can comprise a detector device for detecting at least one of said monitoring particle beams. Even more preferred, said at least one detector device is arranged downstream.

Using the information, which can be obtained by such a detector device, the control of at least one of the particle beams can be enhanced. Additionally and/or alternatively it is possible, to enhance the precision (in particular the measuring precision) of the device. For this, usual feedback algorithms can be used. If the monitoring particle beam is used for gaining information, it is usually possible to get information about the actual position of certain structures within the workpiece. This is particularly true, if the workpiece or parts of the workpiece are moving. Preferably the detector is arranged down-stream to the workpiece. This way, the measurements are taken after the respective particle beam, in particular the monitoring particle beam, has penetrated the workpiece. However, detectors on the windward side of the workpiece can prove to be very helpful as well. A predominant example for this is a detector for measuring the number of particles per unit time (particle flux). In particular, it is possible to take at least one detector device from the group comprising particle energy detectors, particle location detectors, particle type detectors, particle deflection detectors, particle charge detectors, particle velocity detectors, particle direction detectors, particle beam width detectors and/or particle beam intensity detectors. First experiments have shown that particularly detectors of the mentioned types are particularly well suited for gaining usable information. In particular, it is possible to design at least some of the above-mentioned (and even different types of) detectors in a way that they are at least in part and/or at least at times time sensitive and/or position sensitive (in particular they can be one-dimensional position sensitive, two-dimensional position sensitive, three-dimensional position sensitive and/or four dimensional position sensitive).

According to a preferred embodiment of the particle beam generating device, at least one feedback unit is provided, wherein at least one property of at least one of the generated particle beams, preferably of at least one monitoring particle beam is used for controlling at least one of the generated particle beams, preferably for controlling at least one processing particle beam. This way, the quality of the treatment and/or the preciseness (in particular the measurement preciseness) can be enhanced significantly. In particular, the preciseness of the radiation dose introduced into the workpiece can be enhanced. For the feedback unit, usual methods and/or devices can be employed. For instance, standard controllers or standard computers can be used.

Even more preferred, the particle beam generating device can be designed in a way that said particle beam generating device, preferably said feedback unit is designed and arranged in a way that at least one of the generated particle beams can be controlled according to the movement of at least one part of said workpiece, being processed by at least one of said particle beams. This way, it is possible to apply a radiation treatment for moving targets in a very precise way. In particular this situation can occur in or near a moving organ like the lung or the heart. A particular advantage is that the monitoring beam "sees" the density of the penetrated material in that similar way as the processing beam does. This way, the complexity introduced by the non-linear relation between relative biological effectivity and physically deposited radiation dose (which is caused by elongation, compression and rotation of tissue parts) can be introduced into the control of the particle beams in a very elegant way. Even if no treatment beam is (currently) present, the use of such a feedback device can prove to be advantageous, in particular by an enhancement of the measurement quality, as an example.

Another preferred embodiment of the particle beam generating device is achieved if the emission unit of the particle beam generating device is de-signed and arranged in a way that at least one of said particle beams is delivered at least in part and/or at times to ambient pressure. This way, the machine shop and/or the treatment room can be under normal atmospheric conditions. This, of course, enhances the variety of possible applications significantly. Such an emission unit can be realised by using refractive gates, for example.

Another preferred embodiment of the particle beam generating device can be achieved if at least a part of at least one accelerator unit is used at least at times for accelerating particle beams of a different type. This way, the overall complexity of the particle beam generating device can be reduced. In particular, it is possible to use a single accelerator for performing the acceleration to the highest energy level. Usually, this part of the accelerator device is the most complex and hence most expensive. Thus, the cost involved can be reduced significantly.

It is preferred, if said particle beam generating device is designed, at least in part, as a particle beam treatment device and/or as a diagnosing device, preferably for medical and/or veterinary purposes. Recently, particle beam generating devices have proven to be extremely useful for treating cancer. This way, the particle beam generating device of the suggested type can be used for performing such (and even more) treatments.

Another preferred embodiment of the particle beam generating device can be achieved if said particle beam generating device comprises at least one particle mixing device and/or at least one particle fragmenting device. By using a particle mixing device, the two (or more) different types of particles can be generated by different sources. For example, an ion source for heavy ions, as well as a (separate) ion source for protons or helium ions can be provided. The ions, produced by the respective sources are "combined" into a single track. This combination can take place at any point. Preferably, this "mixing" takes place before acceleration, in particular before the final acceleration of the particles. It is also possible to use at least one particle fragmenting device. This can be an intermediary target, where a fraction of the particles of the processing beam is fragmented into smaller parts by nucleonic fragmentation.

Yet another preferred embodiment can be achieved, if the particle beam generating device comprises at least one lateral deflection unit and/or at least one energy variation unit. The lateral deflection device can be a pair of electromagnetic coils (which are preferably arranged perpendicularly). The energy variation device can be of a movable wedge type. The wedge, made of an energy absorbing material is moved in a way that the particle beam has to pass through the wedge for different lengths, thus losing a different amount of energy. This way, the energy of the particle beam can be varied and hence the position of the Bragg-peak can be changed in the longitudinal direction. In particular, by using such a design, scanning techniques, in particular raster scanning techniques can be applied, in particular in combination with a pencil sharp particle beam.

Furthermore, a method for controlling a particle beam device is suggested, wherein at least in part and/or at times two particle beams of a different type are generated, wherein a first type of particle beam is used for processing purposes, in particular for processing a workpiece to be processed, while at least a second type of particle beam is used for monitoring purposes, in particular for monitoring said workpiece. A method of the suggested type will show the same features and advantages as previously described, in analogy. It is possible to modify the basic method in the sense of the previous description. Thus, the additional features and their advantages and characteristics, as already described, can be achieved as well.

Herewith a rasterscanning method can be performed, wherein the at least two particle beams can be scanned in three dimensions across the work-piece or a tumor of a patient. In particular an intensity controlled rasterscanning method can be performed in order to irradiate a target volume inside the workpiece or patient. A precise 3D-dose application of at least one of the particle beams inside the target volume can be controlled by using the second one of the at least two particle beams in order to detect a movement or motion of the target volume. Herein correction means can be used to adapt the position of the particle beam inside the workpiece or patient according to the detected movement or motion. Preferably the correction means are fast correction means. The second particle beam can be used to control the movement of the target volume in real time simultaneously with the irradiation of the moving target volume. Preferably the second particle beam used for detecting the motion of the target volume has a lower intensity as the first particle beam (process beam). The advantage can be found in a low dose exposure compared to other detection methods such as CT-measurements and fluoroscopy.

Additionally or alternatively, a method for measuring the current position of at least one part of at least one workpiece that is at least partially moving with time is suggested, wherein the residual energy of at least one particle beam after passing said workpiece is used at least in part and/or at least at times for determining the current position of at least one part of said at least one workpiece. Even such a method will show the same features and advantages as previously described, in analogy. It is possible to modify the basic method in the sense of the previous description. Thus, the additional features and their advantages and characteristics, as already described, can be achieved as well.

The method can include the calculation of the range of the particle beam passing the workpiece or patient without being stopped from the measured residual energy or measuring the residual range and calculating the residual energy therefrom. Additionally the method can include the measurement of the lateral position. The method preferably combine the measured residual range and the measured lateral position of the particle beam passing the workpiece of the patient. From these detected and/or calculated data an actual composition of the material of the workpiece or the tissue of a patient at each irradiated position can be determined. With that changes in the thickness of layers caused by the movement or motion of the target volume dependant on time can be determined. The method can further include the comparison of layer thicknesses measured during the irradiation and layer thicknesses for different motion states measured or determined before the irradiation. From this the actual motion sate during the irradiation can be determined in real time and the particle beam (process beam) can be adapted accordingly.

In FIG. 1, a particle beam generating device 1 is shown schematically. The particle beam generating device 1 is used to irradiate a workpiece and can also be called a particle beam generating device 1. The particle beam generating device 1 can be principally divided into several functional groups. Firstly into the ion supply group 2, secondly into the accelerator group 3 and thirdly into the beam delivery group 4.

The ion supply group 2 consists in the presently shown example of ion sources 5, 6. The ion sources 5,6 can be of the same type, for example an ECR—Ion Sources. The ion sources 5,6 can as well be of different types, wherein the first ion source 5 (the processing ion source 5) is used for delivering heavy ions like carbon ions, oxygen ions or neon ions. The ions produced by first ion source 5 (processing ion source) will eventually form the processing particle beam 12 (the treatment particle beam), whose function will be explained later on.

The second ion source 6 (monitoring ion source 6) can be used for generating light ions, in particular protons and helium ions. The ions, produced by the second ion source 6 will eventually form the monitoring particle beam 13 (as explained later on).

The two different types of ions, generated by both ion sources 5, 6 will be joined together in mixing chamber 7. This way, two ion beams 12, 13, each being formed of different particles are created. However, the two ion beams 12, 13 will run along the essentially same path. Furthermore, after mixing chamber 7, the same components for accelerating, bending and modulating will be used for both particle beams 12, 13. Therefore, in FIG. 1 only a single line is drawn for both ion beams 12, 13.

The second beam 13 can as well be producted by other means. One possibility is the fragmentation of the first particle beam 12 in a fragmentation target (not shown).

After having been mixed in the mixing chamber 7, both particle beams 12, 13 are initially accelerated by a linear accelerator (linac) 8. In this linear accelerator 8, the particles will be accelerated to approximately 10% of the speed of light (which is a typical value that can easily differ). After being initially accelerated, the particle beams 12, 13 are bent by some bending magnets 9 and are introduced into the synchrotron 10, which will perform the major acceleration for the particles within the accelerator group 3. In the synchrotron 10, the particles will be accelerated in a first step. In a second step, the particles are stored in the synchrotron 10 (functioning at this time as a storage ring) and are slowly extracted by an extraction septum 11. The extraction phase (the so-called particle spill) is typically some 5 to 10 seconds long.

After being extracted from the synchrotron 10, both particle beams 12, 13 will be led to a treatment room 14, in which a workpiece or a patient 15 is arranged. In case of a patient 15, the patient 15 is fixed on a patient table (not shown in FIG. 1).

Before the particle beams 12, 13 will enter the treatment room 14, they will first pass through a bending magnet arrangement 16, with which the particle beams 12, 13 can be bent laterally. This way, different coordinates in the X-Y-plane can be reached by the particle beams 12, 13 (lateral bending). After the bending magnets 16, called scanner-magnets 16 the particle beams 12, 13 will pass through an energy modulator 17. An energy modulator 17 as such is known in the state of the art. As an example, the energy modulator 17 may be comprised of two wedge shaped blocks 18, made of energy absorbing material. The wedges 18 can be moved back and forth, using fast actuators. Depending on the position of the wedges 18 relative to the particle beams 12, 13, the particle beams 12, 13 have to pass a different length through the energy absorbing material of the wedges 18. Hence, the energy of the particle beams 12, 13 can be attenuated within certain limits. This will change the position of the Bragg-peak of the particle beams 12 in the longitudinal direction (Z-direction).

Downstream of the energy modulator 17, the particle beams 12, 13 will pass through a first arrangement of detectors 19. The first set of detectors 19 is arranged upstream to the patient 15. The first set of detectors 19 will, for example, verify the current position of the particle beams 12, 13, will verify the particle energy, leaving the energy modulator 17 (which determines the position of the Bragg-peak in the longitudinal direction within the patient 15), will measure the particle beams 12, 13 intensity and so on.

The particle beams 12, 13 will be released from the vacuum part of the Particle generating device 1 through a window 20. Preferably the window 20, which is as well called emission unit 20 is arranged before a first of arrangement of detectors 19. Wherein previously, the particle beams 12, 13 were routed within vacuum, they are now routed through ambient pressure (approximately standard atmospheric pressure at room temperature).

The first particle beam 12 will be controlled in a way so that the volume to be treated within the patient 15 will be successively scanned with the help of the bending magnets 16 and the energy modulator 17 (preferably using scanning techniques, more preferably raster scanning techniques). This way, a certain radiation dose, as prescribed by a physician, will be deposited in the different areas of the patients' 15 tissue. Therefore, the first particle beam 12 can be referred to as a processing particle beam 12, i.e. the particle beam, performing the "real" treatment. Since the processing particle beam 12 will be stopped at the position of the Bragg-Peak and "get stuck" within the patient 15, this beam will typically not leave the patient 15 on the downstream side behind the patient 15 (seen in the direction of the beam 12).

The situation is different with the second particle beam 13, consisting of lighter ions, such as protons or helium ions. Since the particles of the second particle beam 13 have a lower mass and charge, as compared to the particles of the first particle beam 12, they will usually be not slowed down as fast as the particles of the first particle beam 12. Therefore, the particles of the second particle beam 13 will usually penetrate the patient 15 and leave the patient on the downstream side 15. This can be seen in particular in FIGS. 1 and 2. Although the second particle beam 13 has a different behaviour, as compared to the first particle beam 12 in certain ways (in particular with reference to the penetration length), the particles of the second particle beam 13 still have a similar behaviour like the particles of the first particle beam 12 in other respects. In particular, the density of the tissue penetrated, as seen by the (hadronic) particles of both particle beams 12, 13 is quite similar. Therefore, the imaging and/or tissue information, which can be deferred from the second particle beam 13 is of a high quality than that being used in ion and/or heavy ion particle therapy. Therefore, the second particle beam 13 can be referred to as a monitoring particle beam 13. This monitoring particle beam 13 can be measured downstream to the patient 15, i.e. after having passed the patient's 15 body. This is done with an array of detectors 21 downstream to the patient 15. As already explained, the monitoring particle beam 13 now contains valuable information about the patient's 15 body. This will be further elucidated in FIGS. 3 and 4.

For completeness, it should be mentioned that instead of a patient 15, it is also possible to use a dummy device or a phantom target. The irradiation of the phantom can preferably used as a quality assurance measure. Also, it is possible to irradiate a workpiece like an electronic device with the particle beams 12,13 as an example, a microprocessor, a type of a nano-mechanical device or the like can be modified or structured by the particle beams 12,13.

Furthermore, it is possible to use the beam irradiating device 1 without a "first" particle beam 12 (treatment particle beam 12) i.e. only with a "second" particle beam 13 (monitoring particle beam 13) as well. This can be under-stood in a way that the beam irradiating device 1 is used for a relatively elongated period of time solely with the monitoring ("second") particle beam 13. Using only such a monitoring particle beam 13, the beam irradiating device 1 can be used for measuring and/or controlling the motion of a patient 15. After such a measuring cycle is taken, it is possible to "switch back on" the treatment particle beam 12 (with or without the monitoring particle beam 13). However, it is also possible to use a modified beam irradiating device 1, where no processing ion source 5 is present at all, and hence only a monitoring ion source 6 is present (in the latter case, the mixing chamber 7 can be omitted as well).

Figure 2:
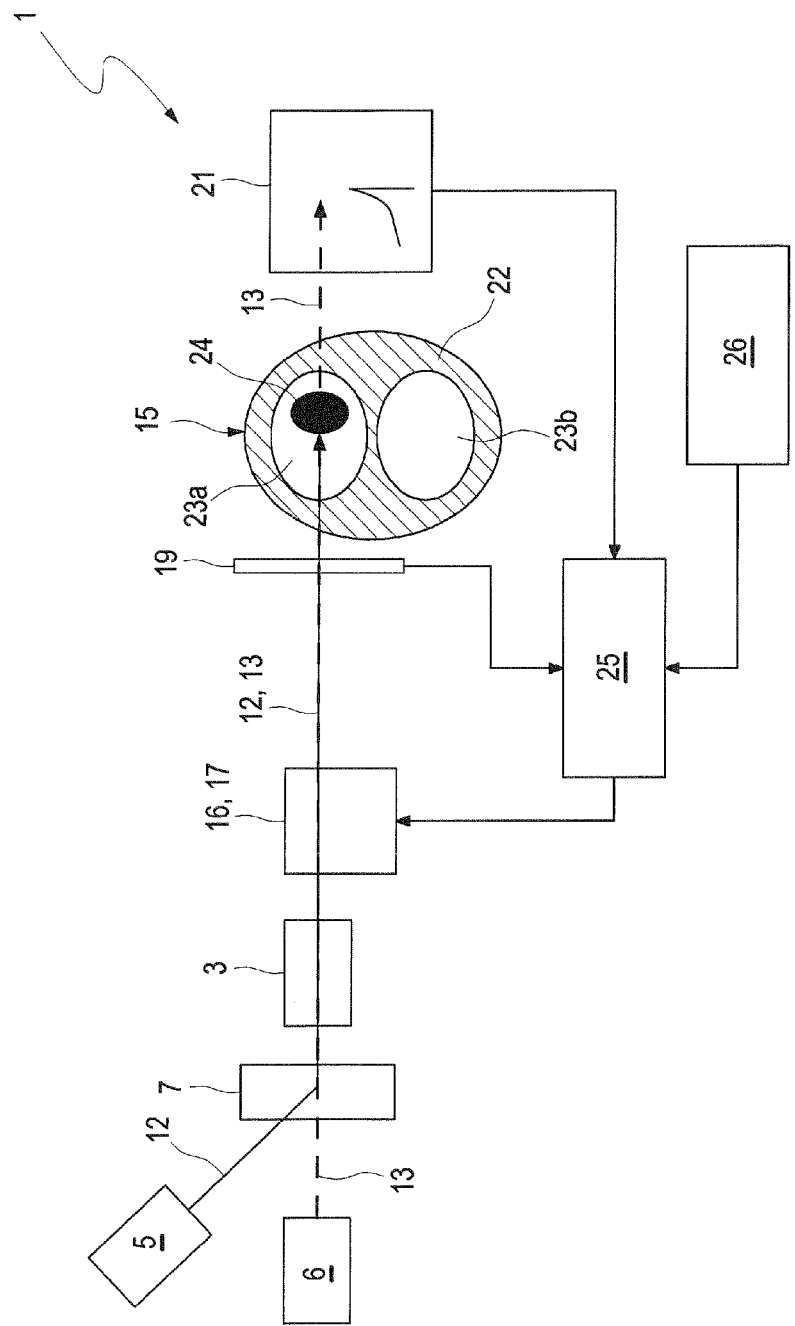
FIG. 2 shows a schematic overview of the treatment section of the particle beam generating device, as shown in FIG. 1.

In FIG. 2, the particle beam generating device 1 is shown once again. This time, however, the figure concentrates on the physical principles and hence FIG. 2 is comparatively abstract. The two particle beams 12, 13, as produced by the two ion sources 5, 6, are joined in the mixing chamber 7. After this, they are passing through the accelerator group 3. Then, the lateral and longitudinal position of the treatment region of the treatment beam 12 is appropriately adapted by the bending magnets 16 and the energy modulator 17. Be-fore being released towards the patient 15, both particle beams 12, 13 first pass through the first set of detectors 19, as previously described. Then, after having passed the patient 15, the monitoring particle beam 13 (and typically only the monitoring particle beam 13!) is measured within the downstream detector array 21.

In FIG. 2, the circumstances within the patient's body 15 are shown in more detail. The patient's body 15 comprises healthy tissue 22, and organs 23 of different nature. In the example shown, the tumour 24 is located on one lung 23a. Reference numeral 23b indicates the other lung. Corresponding to the breathing movement of the patient 15, the tumour 24 is moving accordingly.

As indicated in FIG. 2, only the monitoring particle beam 13 will pass through the patient 15. The first particle beam 12, i.e. the processing particle beam 12, will be controlled in a way, that its location and maximum of the Bragg-Curve is located within the tumour 24. This is done primarily by the bending magnets 16 and the energy modulator 17. By an appropriate control of both units 16, 17, the whole tumour volume 24 can be scanned and therefore treated by scanning techniques.

As it is clear from FIG. 2 (and from the following FIG. 3), the monitoring particle beam 13 contains information about the penetrated tissue. Therefore, this information is fed into a controlling unit 25, which can be a standard computer, for example. However, not only information from the downstream detector 21, but also information from the first set of detectors 19 (i.e. the wind-ward detectors 19) is fed into the controlling unit 25. Another type of information that has to be fed into the controlling unit 25 is the treatment plan 26 and informations about the patient 15. Both are typically determined beforehand (i.e. before the "real" treatment takes place). This bunch of information 26 is also fed into the controlling unit 25 in advance of the treatment. Depending on the information received, the controlling unit 25 will control the bending magnets 16 and energy the modulator 17 accordingly, so that the whole tumour 24 is treated with the particle beam 12 and 13, while movements of the tumour 24 are considered.

Figure 3:
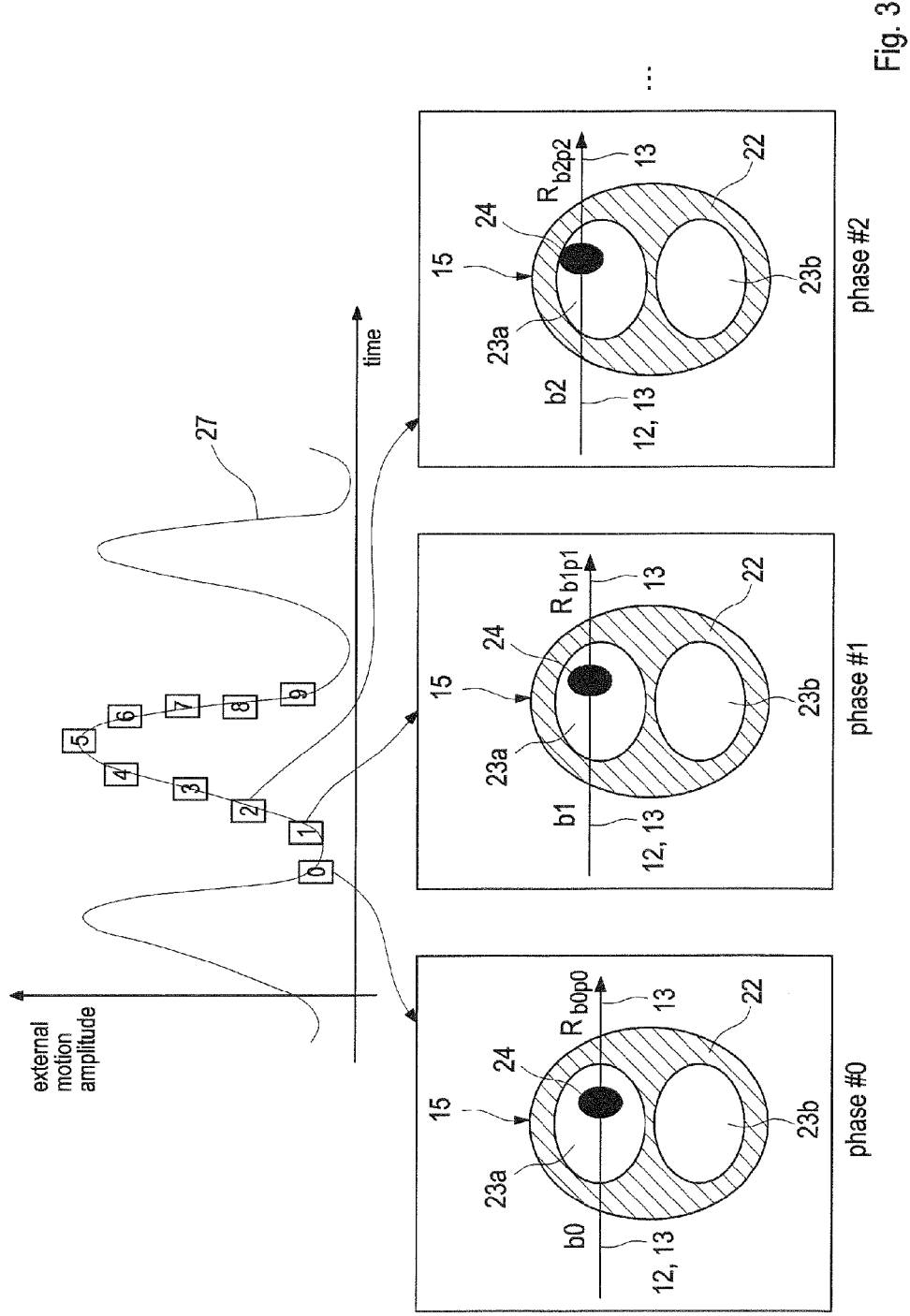
FIG. 3 shows the effects of a moving target in a schematic overview.

In FIG. 3, a typical breathing cycle 27 of a patient 15 is shown. This breathing cycle 27 can be broken down into several phases, as shown in FIG. 3. In the different phases, the tumour 24 will move together with the line 23a. To make the particle beams 12, 13 to follow the movement of the tumour 24, it is possible to monitor the monitoring beam 13 in a way that deviations in its residual energy and/or position (or the like) are measured and an algorithm tries to minimize these deviations. Even by this very simple measure, the tracking quality of the tumour 24 can be very high, since—as already explained—both particle beams 12, 13 are "seeing" the density of the tissue of 15, 23, 24 in a similar way. Wherein the wording "seeing" means that the particle beams 12, 13 penetrating the tissue of the patient 15 where slowed down according to the respective energy loss of the respective particle beam 12, and 13, wherein the particle beam 12 received a higher energy loss than the particle beam 13. Therefore the particle beam 13 can be detected downstream to the patient 15, wherein the remaining energy of particle beam 13 will be slightly different depending on the structure of the tissue. This is due to the fact that basically the same physical interactions are involved with both particle beams 12, 13.

Figure 4:
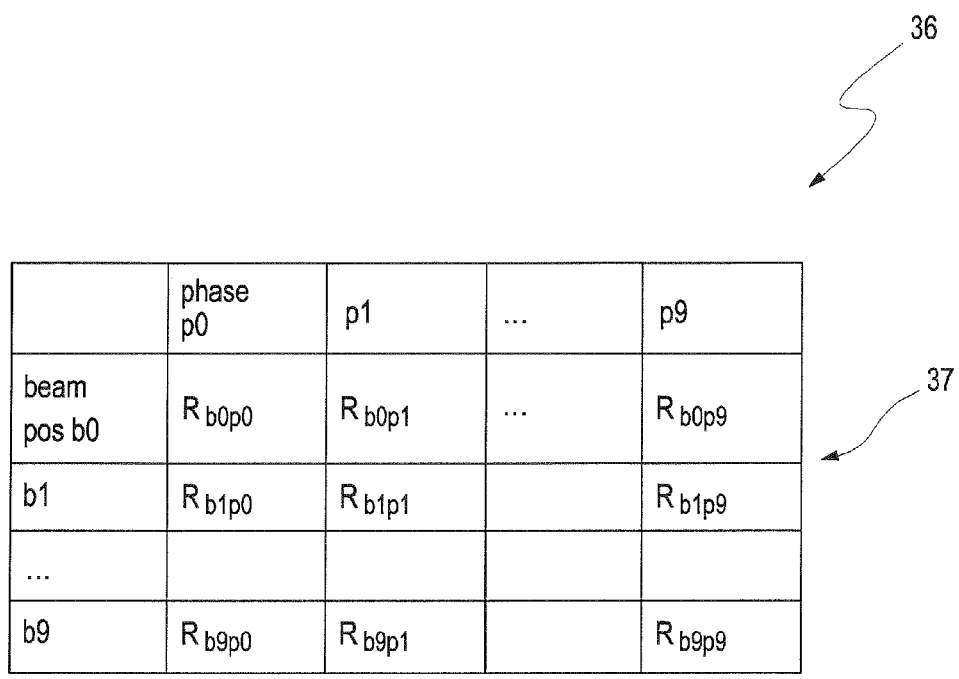
FIG. 4 shows a first embodiment for a method for correlating the particle energy dissipation to the motion phase of the workpiece.

In FIG. 4, a method 36 for correlating the actual movement phase of the tumour 24 during the breathing cycle 27 is schematically shown. This can be done by using a correlation matrix 37, in which for all possible combinations of beam positions "b" and motion phases "p" a range $R_{bp}$ is calculated and stored. In the particular embodiment, shown in FIG. 4, several phases "p0" to "p9", as well as several beam positions "b0" to "b9" are shown. The range $R_{bp}$ is determined experimentally by controlling the respective components of the particle beam generating device 1 appropriately.

Later on, the actual beam position "b" can be preferably measured with a detector 19 that is positioned on the windward side of the patient 15. The range "R" can be measured by measuring the residual energy of the particle beam after passing the patient 15, i.e. by using the downstream detectors 21. Using both numbers "b" and "R", the phase "p" can be derived by using the matrix 37 as a look up table (LUT). In addition to this, plausibility checks can be performed, if several suitable correlating parameters "R" should exist; the one with a phase number "p" that is closest to the previous phase number "p" is usually the most suitable.

Figure 5:
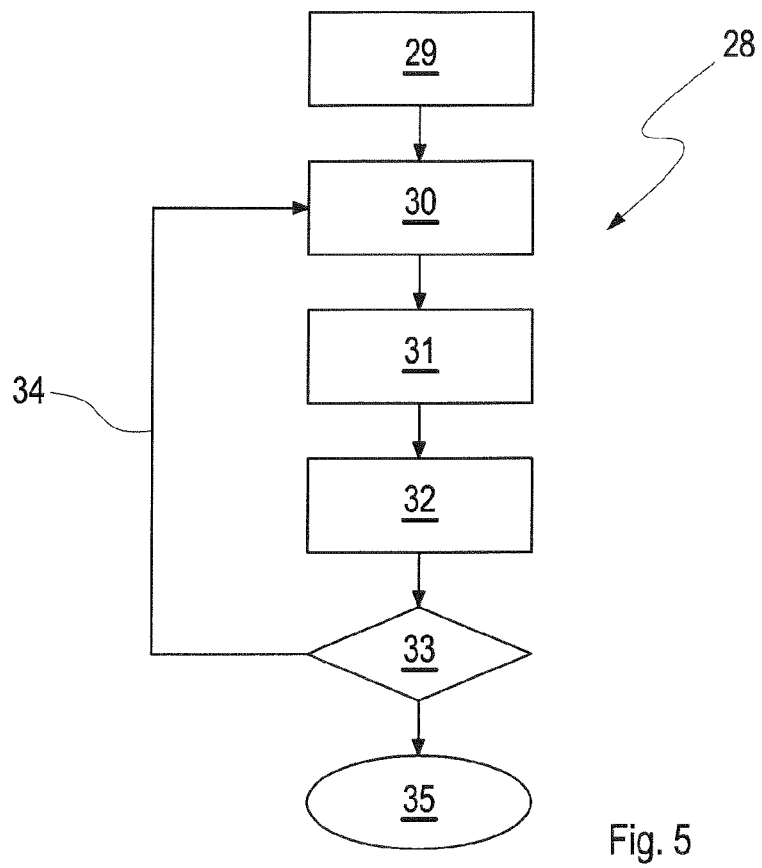
FIG. 5 shows a method for controlling a particle beam generating device in a schematic flow diagram.

In FIG. 5, finally, a method 28 for controlling a particle beam generating de-vice 1 is schematically shown. First, a treatment plan 26 and further informations about a patient 15 to be treated is loaded into a controlling unit 25 in a preparatory step 29. Parallel to this, the patient 15 can be placed on the patient table. Other additional preparatory steps may be taken during this preparatory step 29.

Then, the particle beams 12, 13, i.e. the processing particle beam 12 and the monitoring particle beam 13 are generated 30 and applied to the patient 15.

During this beam generating and application phase 30, the properties of the particle beams 12, 13, both on the upstream side and downstream to the patient 15 (only monitoring beam 13) are measured in a measuring step 31. Based on the information, gained in this measuring step 31, correcting information (for example correcting data for controlling the bending magnets 16 and the energy modulator 17) are calculated in a correcting step 32.

Now, it is checked in step 33, whether the treatment plan has been already completely delivered. If this is not the case, the process steps back to the application phase 30, show with line 34 in particular with, the corrective information. Once again, beams are generated in step 30, measured in step 31, corrected in correcting step 32 and applied to the patient If, however, the treatment plan is already completely delivered, the treatment is finished and the treatment process is stopped 35.

Figure 6:
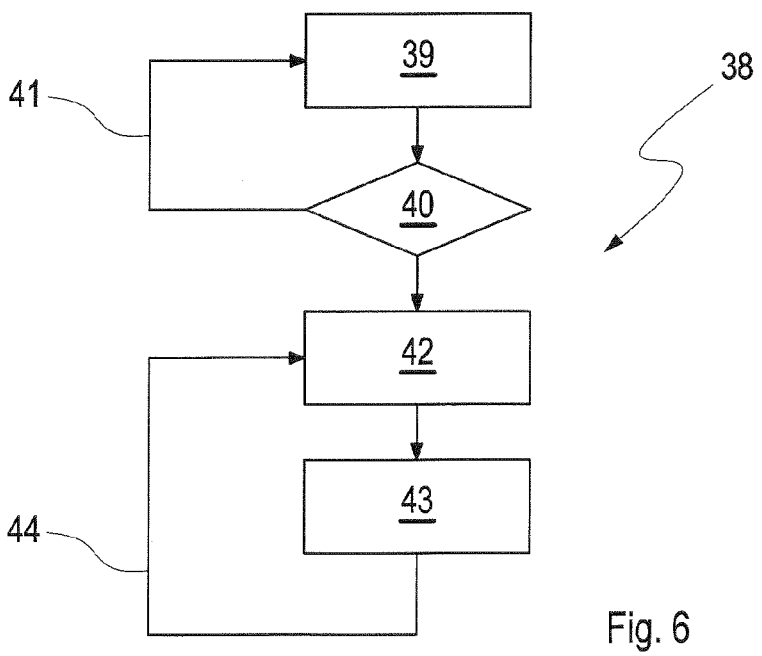
FIG. 6 shows a method for measuring the position of a moving target in a schematic flow diagram.

In summary during the method 38 the calculated ranges Rbp as well as the beam positions b and the phases p are stored n the correlation matrix 37 and correlated with the respective measured range R at a certain beam position b. Finally, in FIG. 6, a method 38 for determining the motion phases of the patient 15 is shown in a schematic flow diagram.

In the initial step 39, for the current pair of motion phase "p" and beam position "b", a correlation number Rbp is stored in a correlation matrix 37, for ex-ample (compare with FIG. 4).

After the actual corresponding parameter Rbp has been stored, in a consecutive update step 40 it is first checked, whether all possible pairs of motion phase "p" and beam position "b" have been measured. If this is not the case, the motion phase "p" and/or the beam position "b" is updated to the next position to be measured, and the program jumps back 41. If the measuring cycle is completed, however, the method 38 enters another loop. Now, in an "input step" 42, the program "listens" to a corresponding parameter Rbp (which is measured in form of a particle beam energy dampening), as well as to a current beam position "b" (which can be measured by position detector 19, 21, preferably by a upstream detector 19 of the patient 15). If such a data pair is acquired, the program derives the corresponding phase "p" from the correlation matrix 37, and outputs the respective value in the following step 43. Having done this, the program jumps back indicated with line 44 and the "listens" to another data input in step 42. In summary the method comprises the steps of finding in the LUT the corresponding Phase p and beam position b from the correlation matrix 37 to a measured range R.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

REFERENCE LIST 1 particle beam generation or irradiating device
2 ion supply group
3 accelerator group
4 beam delivery group
5 ion source (processing)
6 ion source (monitoring)
7 mixing chamber
8 linear accelerator
9 bending magnet
10 synchrotron
11 extraction septum
12 processing particle beam
13 monitoring particle beam
14 treatment room
15 patient
16 bending magnet
17 energy modulator
18 wedges
19 upstream set of detectors
20 window
21 downstream detectors
22 healthy tissue
23 organ
24 tumour
25 controlling unit
26 treatment plan
27 breathing cycle
28 method for particle treatment
29 preparatory step
30 beam generation step
31 measuring step
32 correcting step
33 check for status
34 backward step
35 stop
36 correlating method
37 correlating matrix
38 motion determining method
39 measuring correlation parameter
40 update
41 jump back
42 input step
43 phase deriving step
44 jump back

The invention claimed is:

1. A particle beam generating device, comprising:
at least one accelerator unit for generating a first particle beam that is a processing beam used for processing a workpiece and a second particle beam that is a monitoring beam used for monitoring purposes;
at least one emission unit for the output of the first particle beam and the second particle beam onto the workpiece; and
at least one detector device configured to detect the second particle beam after the second particle beam has penetrated and left the workpiece;
wherein the first particle beam and the second particle beam run along a same path within the accelerator unit and comprise hadronic particles with at least one of a different mass or a different charge.

2. The particle beam generating device according to claim 1, wherein information, gained by the at least one detector device, is at least partially used for determining the current position of the at least parts of the workpiece.

3. The particle beam generating device according to claim 1, wherein at least one of the particle beams contains at least one of nucleonic particles or charged particles.

4. The particle beam generating device according to claim 1, wherein particles of the first particle beam comprise a different energy than particles of the second particle beam.

5. The particle beam generating device according to claim 1, wherein the at least one detector device is taken from the group consisting of particle energy detectors, particle location detectors, particle type detectors, particle deflection detectors, particle charge detectors, particle velocity detectors, particle direction detectors, particle beam width detectors and particle beam intensity detectors.

6. The particle beam generating device according to claim 5, further comprising at least one feedback unit, wherein at least one property of at least one of the generated particle beams is used for controlling at least one of the generated particle beams.

7. The particle beam generating device according to claim 6, wherein the particle beam generating device is designed and arranged in a way that at least one of the generated particle beams can be controlled according to the movement of at least one part of the workpiece, being processed by at least one of the particle beams.

8. The particle beam generating device according to claim 1, wherein the emission unit is designed and arranged in a way that at least one of the particle beams is at least partially delivered to ambient pressure.

9. The particle beam generating device according to claim 1, wherein the at least a part of at least one accelerator unit is used at least at times for accelerating particle beams of a different type.

10. The particle beam generating device according to claim 1, wherein the particle beam generating device is designed, at least in part, as at least one of a particle beam treatment device or as a diagnosing device.

11. The particle beam generating device according to claim 1, further comprising at least one of a particle mixing device and a particle fragmenting device.

12. The particle beam generating device according to claim 1, further comprising at least one of a lateral deflection unit or an energy variation unit.

13. The particle beam generating device according to claim 1, wherein the at least one detector device is arranged on a leeward side of the workpiece.

14. The particle beam generating device according to claim 1, wherein the two particle beams are joined in a mixing chamber.

15. A method for controlling a particle beam processing device, wherein two particle beams, of a different type are generated, wherein a first type of particle beam is used for processing purposes, in particular for processing a workpiece to be processed, while at least a second type of particle beam is used for monitoring purposes, in particular for monitoring the workpiece, wherein the two particle beams run along a same path within an accelerator unit and comprise hadronic particles of at least one of a different mass or a different charge, and wherein at least one detector device detects the second type of particle beam after the second type of particle beam has penetrated and left the workpiece.

16. The method according to claim 15, wherein the residual energy of at least one particle beam after passing the workpiece is used for determining the current position of at least one part of the at least one workpiece.

17. The method according to claim 15, wherein the two particle beams are joined in a mixing chamber.

* * * * *